US012788764B1

(12) United States Patent
Shade et al.

(10) Patent No.: US 12,788,764 B1
(45) Date of Patent: Nov. 10, 2026

(54) TELOMERASE ACTIVITY ENHANCEMENT ORAL-DELIVERY MICROEMULSION AND METHOD

(71) Applicant: Quicksilver Scientific, Inc., Louisville, CO (US)

(72) Inventors: Christopher W. Shade, Louisville, CO (US); Steven Tieu, Louisville, CO (US)

( * ) Notice: Subject to any disclaimer, the term of this patent is extended or adjusted under 35 U.S.C. 154(b) by 315 days.

(21) Appl. No.: 18/217,747

(22) Filed: Jul. 3, 2023

Related U.S. Application Data

(60) Provisional application No. 63/391,640, filed on Jul. 22, 2022.

(51) Int. Cl.

| | |
|---|---|
| ***A61K 31/573*** | (2006.01) |
| ***A61K 9/00*** | (2006.01) |
| ***A61K 9/107*** | (2006.01) |
| ***A61K 31/58*** | (2006.01) |
| ***A61K 31/7048*** | (2006.01) |
| ***A61K 36/236*** | (2006.01) |
| ***A61K 36/258*** | (2006.01) |
| ***A61K 36/481*** | (2006.01) |
| ***A61K 36/70*** | (2006.01) |
| ***A61K 36/81*** | (2006.01) |
| ***A61K 47/10*** | (2017.01) |
| ***A61K 47/44*** | (2017.01) |

(52) U.S. Cl.

CPC .......... *A61K 31/573* (2013.01); *A61K 9/0053* (2013.01); *A61K 9/1075* (2013.01); *A61K 31/58* (2013.01); *A61K 31/7048* (2013.01); *A61K 36/236* (2013.01); *A61K 36/258* (2013.01); *A61K 36/481* (2013.01); *A61K 36/70* (2013.01); *A61K 36/81* (2013.01); *A61K 47/10* (2013.01); *A61K 47/44* (2013.01)

(58) Field of Classification Search

None

See application file for complete search history.

(56) References Cited

U.S. PATENT DOCUMENTS

| | | | | |
|---|---|---|---|---|
| 5,770,578 | A | 6/1998 | Binder et al. | |
| 6,045,801 | A * | 4/2000 | Miyauchi | C07K 14/415 530/370 |
| 7,846,904 | B2 | 12/2010 | Harley et al. | |
| 8,759,304 | B2 | 6/2014 | Harley et al. | |
| 9,248,088 | B2 | 2/2016 | Harley et al. | |
| 10,842,805 | B2 | 11/2020 | Gao | |
| 2011/0218161 | A1 | 9/2011 | Han et al. | |
| 2014/0141082 | A1 | 5/2014 | Gao | |
| 2016/0199398 | A1 | 7/2016 | Gao | |
| 2017/0333337 | A1 | 11/2017 | Frey | |

FOREIGN PATENT DOCUMENTS

| | | | |
|---|---|---|---|
| CN | 101225424 | B | 5/2013 |
| CN | 111759856 | A | 10/2020 |
| EP | 2199402 | A1 | 6/2010 |
| EP | 3229773 | A1 | 10/2017 |
| FR | 3029418 | A1 | 3/2018 |
| JP | 2010538621 | A | 9/2013 |
| WO | 2009046620 | A1 | 4/2009 |
| WO | 2016092193 | A1 | 6/2016 |

OTHER PUBLICATIONS

Deng, Bo , et al., "Radix Astragali-Based Chinese Herbal Medicine for Oxaliplatin-Induced Peripheral Neuropathy: A Systematic Review and Meta-Analysis", Deng, et al., Evidence-Based Complementary and Alternative Medicine, vol. 2016, Article ID 2421876, Aug. 7, 2016, 14 pages.

Qing, Lin-Sen , et al., "Astragalosidic Acid: A NewWater-Soluble Derivative of Astragaloside IV Prepared Using Remarkably Simple TEMPO-Mediated Oxidation", NPL_Qing, et al., MDPI,, Jul. 31, 2017, 7 pages.

* cited by examiner

*Primary Examiner* — Michael V Meller

(57) ABSTRACT

An intra-oral, liquid, microemulsion is provided that is designed to produce telomerase activity enhancement in the cells of subjects through the oral administration of non-derivatized alcohol-soluble deliverables. The intra-oral, liquid, microemulsion includes at least one monolayer surfactant bound droplet and a continuous phase. The monolayer surfactant bound droplets are carried by the continuous phase and preferably deliver an effective amount of the alcohol-soluble deliverables to the bloodstream of a subject. Methods of making and of administering the microemulsion designed to produce telomerase activity enhancement in the cells of subjects when orally administered also are described. Unlike conventional topical oils and creams having viscosities in the greater than 2000 cp range, the intra-oral microemulsion is ingestible, edible, and preferably has a viscosity in the 250 cp to 270 cp range.

36 Claims, 5 Drawing Sheets

TELOMERASE ACTIVITY ENHANCEMENT ORAL-DELIVERY MICROEMULSION AND METHOD

REFERENCE TO RELATED APPLICATIONS

This application claims the benefit of U.S. Provisional Application No. 63/391,640 entitled "Telomerase Activity Enhancement Oral-Delivery Microemulsion and Method" filed Jul. 22, 2022, which is incorporated by reference in its entirety.

BACKGROUND

The tissues of the body and the body's regulation systems become less healthy or functional with age, respectfully. With rare exception, such as Ponce de Leon, most believe that such degeneration is inevitable. However, it is now generally believed that some lifestyle choices and nutritional supplements may be able to slow the degenerative process.

One compound class found in nature credited with regenerative abilities regarding cardiovascular function, mitochondrial function, and more recently telomerase activity enhancement are extracts of the Radix *Astragali* root of the *Astragalus* plant having a tetracyclic triterpenoid chemical structure. Positive benefits associated with Radix *Astragali* root extracts also include anti-inflammatory, immunoregulation, improving blood flow to the heart and brain, and protecting and improving the condition of the liver, kidney, and pancreas. Radix *Astragali* extracts have been used as one of the primary tonic herbs in traditional Chinese and Japanese Kampo medicine.

The Radix *Astragali* root extract astragaloside IV may be hydrolyzed with acid to produce cycloastragenol. Regarding telomerase activity enhancement, Astragaloside IV is attributed with supporting telomerase expression in immune cell populations and may stave off the decline in immune system function that occurs with age. In contrast, cycloastragenol is attributed with supporting telomerase expression in neuronal cells, thus supporting neuronal integrity. Thus, due to the potential ability of Radix *Astragali* root extracts to positively affect age-related cell degeneration through "telomerase lengthening", telomerase activity enhancement has been a recent focus regarding increasing the bioavailability of Radix *Astragali* root extracts.

Telomerase is a ribonucleoprotein that catalyzes the addition of telomeric repeats to the ends of telomeres. Telomeres are long stretches of repeated sequences that cap the ends of chromosomes and are believed to stabilize the chromosome. However, the telomere length of cells decreases each time the cell replicates. Thus, with age, and as the number of times the cell replicates increases, a progressive shortening of the telomeres occurs eventually resulting in the cells entering a senescence stage where they cannot effectively replicate through mitosis and die.

There is evidence to suggest that if the length of the age-shortened telomerase gene is increased, the increased telomere length will allow the cell to more readily divide and create new cells, thus restoring the cell's ability to replicate at a normal or "youthful" rate. Therapeutically produced telomerase activity enhancement has been suggested to occur through the pathway of causing overexpression of hTRT, the gene encoding the protein component of human telomerase, or by causing the expression of proteins that mediate assembly of telomerase. Both the drug Saquinavir, a protease inhibitor, and nitric oxide precursors are believed to operate through these pathways. Benefits expected to be realized by telomerase activity enhancement in a cell or tissue include, for example, enhancement of the replicative capacity and/or life span of said cell or cells within said tissue.

However, Radix *Astragali* extracts, including the more commonly available astragaloside IV (a monomer saponin) have very poor solubility in water, very poor dissolution in gastrointestinal fluids, and an associated low bioavailability. Attempts have been made to improve the water solubility, and associated bioavailability of astragaloside IV by chemical modification, such as by derivatizing astragaloside IV with hesperidinase or to oxidize an alcohol group of the astragaloside IV molecule into a carboxylic acid.

With the hesperidinase derivatization, a preparation suitable for freeze-drying, thus requiring reconstitution in water before injection, followed by intravenous injection was produced—not a preparation suitable for oral delivery. The bioavailability provided by the alcohol to carboxylic acid derivatization of the astragaloside IV molecule via oral delivery is unknown. With either derivatization, the effect on the total therapeutic effect of the astragaloside IV is unknown. Attempts to increase the water-solubility of astragaloside IV by salt formation have proved unsuccessful.

Attempts also have been made to include Radix *Astragali* extracts into skin creams for topical application to heal wounds or reduce the signs of aging in skin cells by inhibiting cell death during proliferation and thus promoting skin cell growth. Such topical application creams open the possibility of using oil as opposed to water as a solvent for the Radix *Astragali* extracts, but similarly to water, neither astragaloside IV nor cycloastragenol are very soluble in oil. The topicals also introduce the issue of poor transfer through the skin or chemical modification during through skin transfer to the bloodstream. Such topical macro- or pseudo-emulsions are not useful for oral delivery and have viscosities generally greater than 2000 centipoise (cp).

Pregnenolone is an alcohol-soluble hormone precursor in by acting as a precursor for cortisol, estrogen, progesterone, testosterone, and DeHydroEpiAndrosterone (DHEA). Thus, sufficient pregnenolone is necessary for the body to maintain proper hormone balance.

DHEA is an alcohol-soluble steroidal hormone naturally produced in the body by the adrenal gland that the body then converts to other hormones, including DHT, testosterone, and estrogen. Thus, being like pregnenolone as a precursor hormone. Some believe that taking DHEA supplements to maintain DHEA levels could have a positive effect by possibly slowing the aging process and thus improving well-being, cognitive function, and body composition. However, to date research has not confirmed this belief.

Other than by injection or implant, the delivery of non-derivatized hormones to mammalian organisms can be difficult or unwise from a liver toxicity perspective. If delivered orally, conventional delivery systems often result in extensive metabolism of nonderivatized hormone in the liver, which may modify or render the hormone ineffective, and cause undesirable liver stress.

For example, oral delivery of nonderivatized testosterone results in negligible blood concentration of testosterone, as substantially complete "digestion" of the hormone occurs in the stomach and liver-putting stress on the liver. In contrast to testosterone, progesterone and DHEA can be taken orally in solid or suspended form, and if enough is taken orally in solid or suspended form, achieve therapeutically effective bloodstream concentrations. Thus, for progesterone and DHEA, while greater than medically necessary dosages are needed to obtain therapeutically effective bloodstream concentrations, such bloodstream concentration may be orally obtained for these hormones with conventional delivery systems with the potential of increased systematic side effects.

The systemic side effects arising from ingesting greater than medically necessary dosages of nonderivatized hormones in solid or suspended conventional form is often attributable to the significant stress placed on the liver as the majority of these nonderivatized hormones are digested and not initially transferred to the bloodstream. Thus, conventional oral delivery to achieve therapeutically effective bloodstream concentrations is practically non-existent for some nonderivatized hormones, while for others conventional oral delivery results in substantial loss of the hormone- and in either case, undesirable stress is placed on the liver at a minimum, with liver damage being possible. This situation is especially apparent for nonderivatized hormones that are alcohol-soluble and not well-solubilized in water or oil.

Unlike conventional OIW emulsions (oil droplets in a water continuous phase—thus an oil-in-water emulsion), conventional WIO emulsions (water droplets in an oil continuous phase—thus, a water-in-oil or "invert emulsion") have been made with nonderivatized alcohol-soluble hormones. One such example is found in U.S. Pat. Pub. 2009/0069279 (abandoned) to Astruc et al. Astruc describes using nonderivatized dehydroepiandrosterone (DHEA) in an invert emulsion with non-ingestible polar glycolic and hydroglycolic solvents dispersed with silicone-based emulsifiers into an oil medium. The reference recognizes the alcohol—as opposed to oil- or water-soluble nature of nonderivatized DHEA and the difficulty of incorporating nonderivatized DHEA into an OIW emulsion. Such a solubility situation also applies to pregnenolone, which has a similar solubility profile to DHEA. However, the invert WIO systems of Astruc cannot be made for human consumption because of the inedible constituents, thus being limited to dermal application.

For nonderivatized hormones, conventional emulsion delivery systems have traditionally addressed the inability to form OIW emulsions by first derivatizing the alcohol-soluble hormone with ester or related functionality, thus substantially enhancing the oil-solubility of the hormone. The additional alkyl groups of the derivatized hormone provide increased oil-solubility to the hormone, thus permitting the derivatized hormone to dissolve in oils for injection or to be carried by conventional oil-in-water emulsion formulations. As previously discussed, chemical modification to alter solubility has also been attempted to convert alcohol-soluble astragaloside IV into water-soluble molecules by derivatizing astragaloside IV with hesperidinase or a carboxylic acid.

Hence, conventional delivery systems have focused on making Radix *Astragali* extracts more water-soluble and on making nonderivatized hormones more oil-soluble—not on finding an oral delivery system that could solubilize and thus deliver the nonderivatized alcohol-soluble molecules. Thus, the conventional path for increasing the bioavailability of alcohol-soluble deliverables is to chemically modify the deliverable to be more water- or oil-soluble. Water- or oil-soluble derivatized deliverables may be injected IV or IM, respectively, or may be applied topically with OIW invert emulsion creams by placing the derivatized deliverable in the continuous or oil emulsion phase, respectively.

FIG. 1 represents a micelle 100 having a single wall of phospholipids (monolayer) forming a hydrophilic exterior 120 and a hydrophobic interior 110 lacking the hydrophilic capsule interior of a liposome. Thus, in relation to a liposome, a micelle lacks a bilayer and does not provide a liposomal capsule interior that can contain a water-soluble, hydrophilic core composition. The micelle 100 may be thought of as the outer wall of a liposome without the inner wall providing for a capsule interior.

Polyethylene glycol modified vitamin E, such as tocopheryl polyethylene glycol succinate 1000 (TPGS), may be used to form micelles in water as the TPGS has a water-soluble head and an oil-soluble tail. While not shown in the figure, a reverse micelle is formed in a nonpolar continuous phase, as opposed to the "normal" polar continuous phase, which results in the normally hydrophobic interior of the micelle being reversed and the "reverse micelle" having a hydrophilic interior.

FIG. 2 represents a monolayer surfactant where the oil component is associated with the hydrophobic tails of a surfactant. In this representation, the surfactant forms a circular shape, thus encircling the oil component, and approximates a relatively large, expanded micelle. However, such encircling is not required for the oil component to associate with the hydrophobic tails of the surfactant. Nutritional supplements are introduced to the bloodstream in multiple ways. Supplements taken orally are absorbed at different rates, generally due to the different solubilities of the supplements. For example, on average about 10% to 20% at most of a solid supplement preparation including non-water-soluble deliverables taken orally is absorbed. As a specific example, nonderivatized astragaloside IV has an absorption rate less than 3% when taken orally. For oil-soluble supplements this can be increased to about 30% with an orally taken gel capsule, to about 45% with a transdermal patch, and to about 50% with conventional intra-oral (sublingual) administration of an OIW emulsion. However, it is not uncommon for alcohol-soluble deliverables to have oral absorptions less than 1%, with little improvement provided by gel capsules, transdermal patches, or conventional OIW emulsions. Absorption of water-soluble supplements taken orally is generally higher than observed for non-water-soluble supplements, but bioavailability of the water-soluble supplement may still be low if the specific supplement is metabolized by the liver at a rapid rate.

In contrast, injection provides from approximately 90% to 100% bloodstream absorption of a non-water-soluble supplement, but is uncommonly used for nutritional supplements. Thus, while injection can provide immediate and nearly total absorption into the bloodstream, unless the injection is continued for an extended period, thus becoming an infusion, the timeframe in which the nutritional supplements are available to the living cells may be limited. Additionally, if the living cells can only adsorb a relatively low amount of the nutritional supplement per unit time, the high, but time limited nutritional supplement bloodstream concentration resulting from injection may not translate into an effective cellular concentration of the nutritional supplement.

The present invention avoids or ameliorates at least some of the disadvantages of conventional oral supplement preparations intended to affect telomere activation in a subject through the delivery of nonderivatized alcohol-soluble deliverables to the bloodstream.

BRIEF DESCRIPTION OF THE FIGURES

The invention can be better understood with reference to the following drawings and description. The components in the figures are not necessarily to scale and are not intended to accurately represent molecules or their interactions, emphasis instead being placed upon illustrating the principles of the invention.

DETAILED DESCRIPTION

Figure 1:
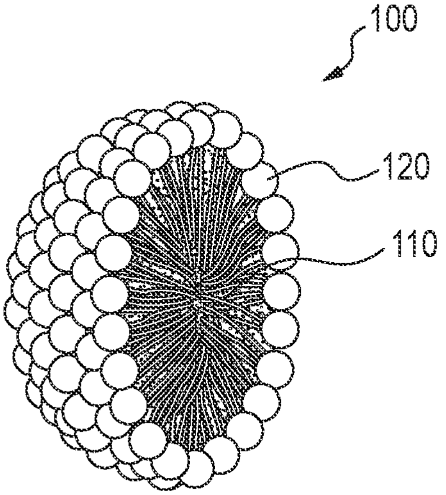
FIG. 1 represents a micelle having a single wall of phospholipids (monolayer) forming a hydrophilic exterior and a hydrophobic interior lacking the capsule interior of a liposome.
Figure 2:
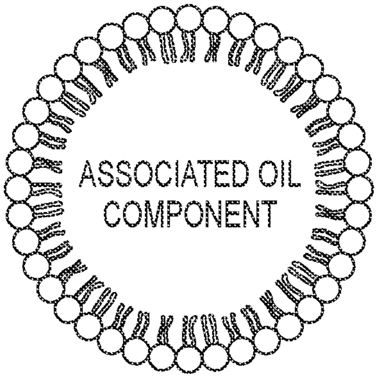
FIG. 2 represents a monolayer surfactant where the oil component is associated with the hydrophobic tails of the surfactant.

An intra-oral, liquid, microemulsion is provided that is designed to produce telomerase activity enhancement in the cells of subjects through the oral administration of nonderivatized alcohol-soluble deliverables. The intra-oral, liquid, microemulsion includes at least one monolayer surfactant bound droplet and a continuous phase. The monolayer surfactant bound droplets are carried by the continuous phase and preferably deliver an effective amount of the alcohol-soluble deliverables to the bloodstream of a subject. Methods of making and of administering the microemulsion are also described. Unlike conventional topical oils and creams having viscosities in the greater than 2000 cp range, the intra-oral microemulsion is ingestible, edible, and preferably has a viscosity in the 250 cp to 270 cp range.

The microemulsion may be thought of similarly to an OIW dispersion, but where the "oil component" of the OIW dispersion is associated with a surfactant system to form monolayer surfactant bound droplets. The monolayer surfactant bound droplets are hydrophobic and are distributed in a polar, and thus hydrophilic, continuous liquid phase. The droplets include nonderivatized alcohol-soluble deliverables combined with an associating oil and alcohol that together assist in associating the alcohol-soluble deliverables with the surfactant system. In this way, the "oil" phase of the microemulsion is modified with alcohol and the surfactant system in relation to a conventional OIW dispersion.

The hydrophobic portion of the monolayer wall of the monolayer surfactant bound droplets is formed from the tails of a phospholipid in combination with a polyethylene glycol derivative. When the phospholipid is used with the polyethylene glycol derivative in the described ratios, a reduction in alcohol loss from the monolayer surfactant bound droplets in relation to conventional OIW dispersions is believed to occur due to the formation of a less porous hydrophobic portion of the monolayer wall.

The retained relatively high alcohol content resulting from the reduced loss of alcohol is believed to increase the solubility of nonderivatized alcohol-soluble deliverables in the monolayer surfactant bound droplets of the microemulsion in relation to the oil phase of conventional OIW dispersions—thus allowing co-delivery of the alcohol-soluble deliverables. This enhanced solubility of the alcohol-soluble deliverables in the monolayer surfactant bound droplets is believed to reduce dissociation (e.g., recrystallization, precipitation, and like—thus separation) of the alcohol-soluble deliverables from the monolayer surfactant bound droplets of the microemulsion and prevent the alcohol-soluble deliverables from not being delivered to the cells in combination.

The constituents and constituent ratios used in the continuous phase of the microemulsion also are believed to assist in allowing the monolayer surfactant bound droplets to incorporate and retain their relatively high alcohol content in relation to the oil phase of conventional OIW dispersions. Thus, the continuous phase is believed to assist in forcing the oil, alcohol, and the alcohol-soluble deliverables into the interior of the monolayer walls of the monolayer surfactant bound droplets, while the polar continuous phase including the sugar or sugar alcohol and water resides external to the monolayer walls.

Unlike the primarily water continuous phase of a conventional OIW dispersion, the sugar or sugar alcohol of the microemulsion's continuous phase does not readily form an azeotrope with alcohol, and thus has a reduced ability to extract alcohol from the monolayer surfactant bound droplets in relation to water. Without the combination of the described monolayer surfactant bound droplets to solubilize the nonderivatized alcohol-soluble deliverables in combination with the described continuous phase, the blood delivery performance, transparency, and shelf-stability of the microemulsion could not be achieved.

Without the monolayer surfactant bound droplets to intra-orally transport the solubilized nonderivatized alcohol-soluble deliverables to the bloodstream, deliverable bioavailability would be extremely poor—as observed with conventional preparations. It is believed that the monolayer surfactant bound droplets allow the nonderivatized astragaloside IV, cycloastragenol, and pregnenolone to be transported to the bloodstream and thus living cells substantially simultaneously, unaltered, and in the desired ratios to maximize telomere activation enhancement. This is believed possible as the monolayer surfactant bound droplets are believed to reduce or eliminate the inconsistent and substantial modification and/or transformation of the deliverables via digestion by the stomach, liver, and intestine that has plagued prior oral delivery systems with each deliverable introduction-without substantial stress on the liver.

Intra-oral consumption of the microemulsion including the monolayer surfactant bound droplets carried by the continuous phase is believed to prevent the extensive metabolism of the alcohol-soluble deliverables observed for conventional, orally-administered supplements whose primary deliverable absorption path is through the gut. Such codelivery of the alcohol- and the water-soluble deliverables to the bloodstream is believed important as without their co-delivery, the potential telomerase activity enhancement attributable to the Radix *Astragali* extracts is expected to be reduced or not result in the desired health benefit.

Additionally, it is believed that without the proper hormone balance and HPA function provided by the pregnenolone, the potentially obtained telomerase activity enhancement available from the Radix *Astragali* extracts will be reduced or not result in the desired health benefit. Thus, the monolayer surfactant bound droplets are believed to allow the alcohol- and any optional oil-soluble deliverables to reach the bloodstream at a rate substantially approximating any water-soluble deliverables present in the continuous phase of the microemulsion—thus providing a combined effect of the different solubility deliverables substantially simultaneously in the bloodstream and thus to the living cells.

The monolayer surfactant bound droplets of the microemulsion also approach injection administration in the rate and concentrations at which the body transfers the alcohol- and any oil-soluble deliverables into the bloodstream via intra-oral delivery. Thus, in addition to the advantage of not requiring venipuncture for relatively rapid and high bloodstream concentration bioavailability of the nonderivatized alcohol and any oil-soluble deliverables, the monolayer surfactant bound droplets are believed to maintain a longer-duration increased concentration of the deliverables in the bloodstream than available from injection, and thus a longer duration, high-concentration availability to the living cells.

The monolayer surfactant bound droplets including the alcohol-soluble deliverables have an average droplet diameter from 10 nanometers to 100 nanometers, preferably from 10 nanometers to 60 nanometers. More preferably, the monolayer surfactant bound droplets have an average droplet diameter from 10 nanometers to 40 nanometers.

An average droplet diameter less than 125-nm is important for the microemulsion, as droplets much larger than this will not transport through the tissues of the mouth, but instead will enter the stomach and be substantially irreversibly chemically altered, thus deactivated/digested by acid and bile salts. The 60 nm average diameter provides transparency to the microemulsion, as average droplet diameters larger than 100 nm provide translucent liquids that degrade into milky liquids if unstable. Thus, the average droplet diameter of the monolayer surfactant bound droplets provides a microemulsion having an optimized intra-oral ability that is transparent and shelf-stable.

As previously described, the monolayer surfactant bound droplets of the microemulsion include a surfactant system, an associating oil, alcohol, and nonderivatized alcohol-soluble deliverables. The surfactant system includes a phospholipid and a polyethylene glycol derivative.

The phospholipid of the surfactant system is a glycerophospholipid preferably isolated from lecithin. As the phospholipid is preferably a lecithin isolate, the named isolates preferably include 80% (w/w) of the specified phospholipid with the remaining constituents being one or more additional phospholipids isolated from the lecithin or other lecithin isolates. The phospholipid constitutes from 3% to 7% of the microemulsion by weight.

Preferred phospholipid lecithin isolates include phosphatidylcholine (PC), phosphatidylethanolamine (PE), phosphatidylinositol (PI), ceramide phosphoryl ethanolamine (Cer-PE), ceramide phosphoryl choline (SPH), and combinations thereof, with PC, PE, and combinations thereof being more preferred. Presently, the phospholipid PC is most preferred in forming the monolayer surfactant bound droplets of the microemulsion. However, all phospholipid lecithin isolates are unexpectedly not interchangeable in forming transparent and shelf-stable microemulsions, as the phosphatidylserine (PS) and phosphatic acid (PA) isolates are not useful when a transparent and shelf-stable microemulsion including monolayer surfactant bound droplets is desired.

The monolayer surfactant bound droplets include a ratio of phospholipid to polyethylene glycol derivative from 1:1.4 to 1:2.5 by weight, preferably from 1:1.8 to 1:2.1 by weight to form the surfactant system. The polyethylene glycol derivative may be a polyethylene glycol modified vitamin E, such as tocopheryl polyethylene glycol succinate 1000 (TPGS), polysorbate 40, polysorbate 60, or polysorbate 80. Preferably, the polyethylene glycol derivate is TPGS, polysorbate 60, or polysorbate 80. More preferably, the polyethylene glycol derivative is TPGS or polysorbate 80, and most preferably at present TPGS. The polyethylene glycol derivative constitutes from 8% to 11% of the microemulsion by weight.

The monolayer surfactant bound droplets include a ratio of phospholipid to associating oil from 1:0.8 to 1:1.4 by weight, preferably from 1:1 to 1:1.3 by weight. The associating oil of the monolayer surfactant bound droplets is selected from the group consisting essentially of medium chain triglycerides (MCT), citrus oil, and combinations thereof. Preferable MCT oils include caproic acid (hexanoic acid), caprylic acid (octanoic acid), capric acid (decanoic acid), lauric acid (dodecanoic acid), and combinations thereof. More preferred MCT oils include caprylic acid, capric acid, and combinations thereof. Preferred citrus oils include orange oil, lemon oil, and combinations thereof. The associating oil constitutes from 2% to 7% of the microemulsion by weight.

The monolayer surfactant bound droplets include a ratio of phospholipid to alcohol from 1:1.8 to 1:2.5 by weight, preferably from 1:2 to 1:2.3 by weight. The alcohol preferably is food grade as the microemulsion is edible. Preferably, the alcohol is ethanol, with USP food grade 190 proof (95% ethanol, 5% water) ethanol being more preferred. Alcohol water contents exceeding 10% are less preferred, as then the additional water should be considered in relation to the total water content of the microemulsion to prevent dissociation of the alcohol-soluble deliverables from the monolayer surfactant bound droplets as discussed further below. The alcohol constitutes from 8% to 13% of the monolayer surfactant bound droplets by weight and from 17% to 22% of the microemulsion by weight when the alcohol contribution from the hybrid-soluble deliverables is included, as discussed further below.

The monolayer surfactant bound droplets include a nonderivatized alcohol-soluble Radix *Astragali* extract and at least one nonderivatized alcohol-soluble hormone. The preferred nonderivatized alcohol-soluble Radix *Astragali* extract is a combination of astragaloside IV and cycloastragenol. The preferred nonderivatized alcohol-soluble hormone is chosen from pregnenolone, DHEA, and combinations of pregnenolone and DHEA. The nonderivatized alcohol-soluble deliverables are directly solubilized into the monolayer surfactant bound droplets.

The astragaloside IV, cycloastragenol, and nonderivatized hormone deliverables are preferably included in the monolayer surfactant bound droplets in a ratio of 1:1:1±20%, preferably +10% by weight. Preferably, the ratio of phospholipid to these alcohol-soluble deliverables is 1:0.08 to 0.17 by weight, more preferably from 1:0.1 to 1:0.15 by weight. Preferably, the ratio of these alcohol-soluble deliverables to the associating oil is 1:6 to 1:11 by weight, more preferably from 1:6.5 to 1:9 by weight. The alcohol-soluble deliverables constitute from 0.6% to 1.2% of the microemulsion by weight.

In addition to directly solubilized nonderivatized hormones, such as alcohol-soluble nonderivatized pregnenolone, derivatized hormones, such as esterified hormones, may be included in the monolayer surfactant bound droplets due to the oil-solubility of the derivatized hormones and the ability of the monolayer surfactant bound droplets to solubilize oil-soluble deliverables in addition to the alcohol-soluble deliverables. For example, such inclusion of derivatized oil-soluble hormones could be advantageous in the event a greater hormone density in the microemulsion or a modified dosing profile is desired as the nonderivatized hormones of the monolayer surfactant bound droplets would be expected to enter the bloodstream more rapidly than their derivatized oil-soluble counterparts.

The continuous phase of the microemulsion that carries the monolayer surfactant bound droplets includes hybrid-soluble deliverables when formed, water-soluble deliverables, a sugar or sugar alcohol, and water.

Hybrid-soluble deliverables include herbal extracts including alcohol-soluble polyphenol constituents and water-soluble constituents, thus being considered a "hybrid" deliverable for solubility purposes as they include both alcohol- and water-soluble deliverables. Hybrid-soluble deliverables include He Shou Wu Tincture, Zhi Gan Cao (Honey prepared Licorice root), and Ashwagandha Liquid Tincture. These hybrid-soluble deliverables are believed to synergically activate and/or potentiate the telomerase activity enhancement of the Radix *Astragali* root extracts and provide more consistent telomerase activity enhancement than when the Radix *Astragali* root extracts are otherwise administered. Other or additional hybrid-soluble deliverables may be included that are compatible with the alcohol-soluble deliverables and do not adversely affect the structure of the microemulsion from a dissociation or average droplet diameter perspective.

Due to the hybrid solubility of these deliverables, they are added into the continuous phase in a solvent system including a 1:1±20% ratio of alcohol to water by weight. When the continuous phase including the hybrid-soluble deliverables is combined with the monolayer surfactant bound droplets during formation of the microemulsion, the alcohol-soluble constituents of the hybrid-soluble deliverables that are insoluble in the continuous phase are believed to solubilize into the monolayer surfactant bound droplets to retain the desired deliverable bioavailability, transparency, and shelf-stability of the microemulsion. Thus, after being added to the continuous phase during formation of the microemulsion, the hybrid-soluble deliverables are believed to partition their constituents between the monolayer surfactant bound droplets and the continuous phase.

Due to the addition of the hybrid-soluble deliverables to the continuous phase, the microemulsion includes alcohol provided by the monolayer surfactant bound droplets as discussed previously and a smaller amount of alcohol by weight arising from the addition of hybrid-soluble deliverables to the continuous phase. The alcohol used in combination with the hybrid-soluble deliverables preferably is food grade ethanol as previously discussed regarding the monolayer surfactant bound droplets. The ratio of alcohol present in the monolayer surfactant bound droplets to that introduced into the continuous phase via the hybrid-soluble deliverables is from 1:0.5 to 1:1.2 by weight, preferably from 1:0.6 to 1:0.9 by weight. The hybrid-soluble deliverables constitute from 2% to 6% of the microemulsion by weight excluding the alcohol and water used to combine them into the microemulsion.

Water soluble deliverables include Ashwagandha in solid powder form, Chinese Ginseng in solid powder form, American Ginseng in solid powder form, and Fermented Korean Ginseng in solid paste form. The water-soluble solid powder form deliverables constitute from 2% to 4% by weight of the microemulsion.

By "sugar or sugar alcohol" it is meant a sugar or a sugar alcohol preferably including from 3 to 12 carbon atoms that is a liquid at room temperature and pressure or is soluble in water at room temperature and pressure. Preferable sugars include allulose, sucrose, cane sugar, and pure maple syrup, with pure maple syrup being preferred due to the inclusion of tree resins. Preferable sugar alcohols have from 3 to 6 carbon atoms and include glycerol (glycerin).

While one could expect additional sugar alcohols, including xylitol, erythritol, mannitol, and sorbitol to be useful in forming the microemulsion, all sugar alcohols are unexpectedly not interchangeable in forming transparent, shelf-stable microemulsions. In fact, xylitol, erythritol, mannitol, and sorbitol are not useful when both transparent and shelf-stable microemulsions are desired. Thus, preferred sugar or sugar alcohols include allulose, sucrose, cane sugar, pure maple syrup, glycerol, and combinations thereof. More preferred sugar or sugar alcohols include pure maple syrup, glycerol, and combinations thereof. Presently, the most preferred sugar or sugar alcohol is glycerol.

When the sugar or sugar alcohol is glycerol, the ratio of glycerol to water (including the water introduced from the hybrid-soluble deliverables) in the continuous phase is from 1:0.3 to 1:0.7 by weight, preferably 1:0.5 by weight with deviations up to 10% by weight being included, thus 1:0.5±10% preferred by weight. When the sugar or sugar alcohol is pure maple syrup, sucrose, or cane sugar, and water is present in the syrup or used to solubilize the sucrose or cane sugar, this additional water becomes part of the water constituent of the continuous phase and is thus included in the sugar or sugar alcohol to water weight ratio as water. The sugar or sugar alcohol constitutes from 32% to 40% of the microemulsion by weight.

The water of the continuous phase is present in the microemulsion from 15% to 21%, preferably from 17% to 19% on a weight basis including the water introduced from the hybrid-soluble deliverables—thus the total water present in the microemulsion.

The ratio of the polyethylene glycol derivative of the surfactant system to the water and the sugar or sugar alcohol of the continuous phase is important to maintain the transparency, average droplet diameter, and shelf-stability of the microemulsion. The preferred ratio of the polyethylene glycol derivative to the water to the sugar or sugar alcohol is 1:2:4±20%, preferably 1:2:4±10% by weight. For example, if the polyethylene glycol content of the microemulsion falls too much in relation to this ratio, the alcohol-soluble deliverables will dissociate. Similarly, increases in the polyethylene glycol content of the microemulsion too far beyond this ratio results in an undesirable viscosity increase beyond the preferred 250 cp to 270 cp range. Insufficient water in relation to this ratio also results in dissociation of the alcohol-soluble deliverables. As previously discussed, the ratio of sugar or sugar alcohol to water is important in preventing alcohol loss from the monolayer surfactant bound droplets that also results in dissociation of the alcohol-soluble deliverables.

The microemulsion may optionally include other ingredients or "adjuvants" that are chemically compatible with the alcohol- and hybrid-soluble deliverables and do not substantially interfere with the separation between the monolayer surfactant bound droplets and continuous phase while not inverting the microemulsion. Such adjuvants may include flavors, preservatives, antioxidants, electrolytes, perfumes, and pigments. Other adjuvants may be used in the microemulsion.

Figure 3:
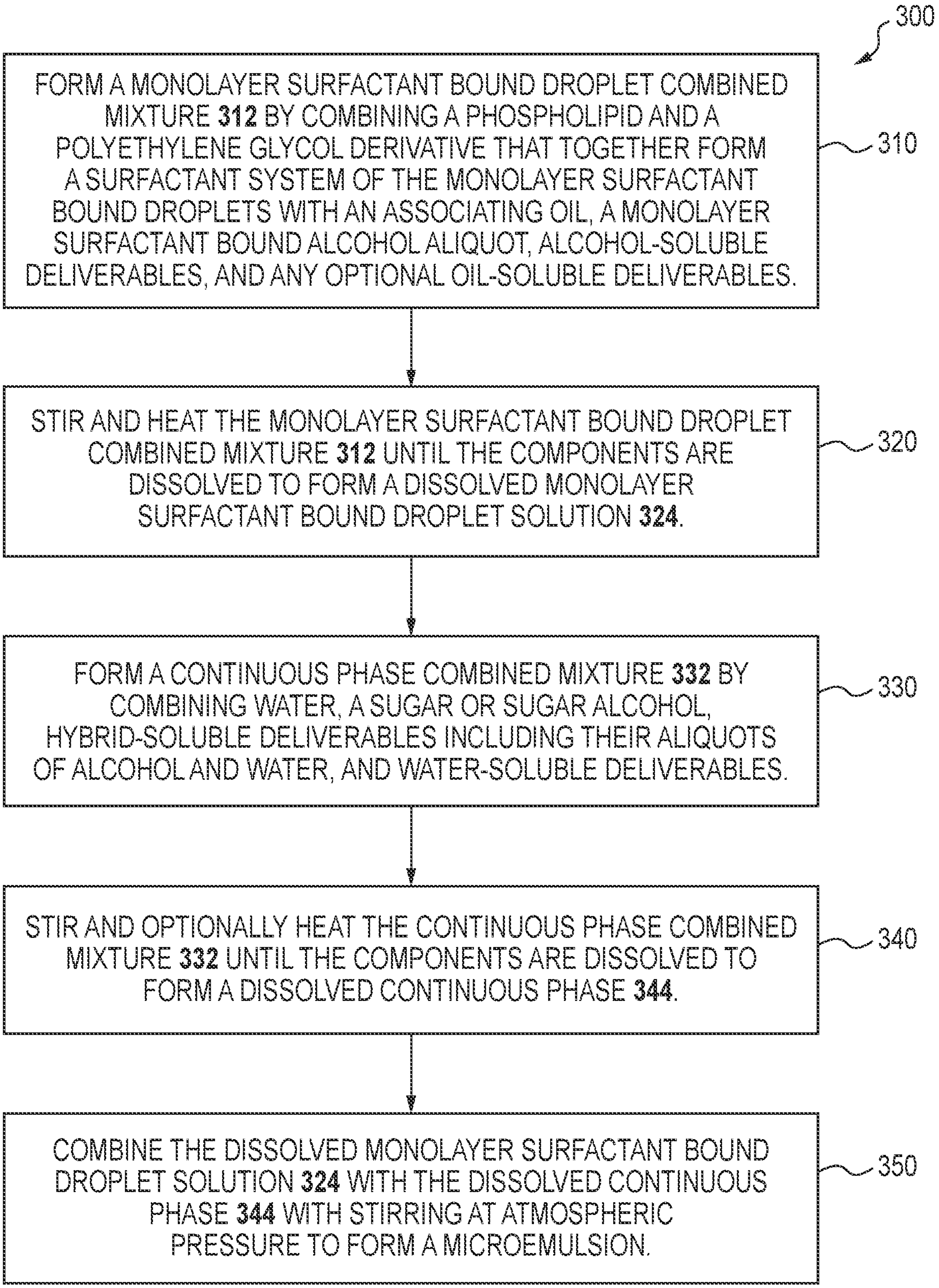
FIG. 3 represents a method of making the microemulsion including the alcohol-soluble, hybrid-soluble, water-soluble, and any optional oil-soluble deliverables.

FIG. 3 represents a method 300 of making the microemulsion including the alcohol-soluble, hybrid-soluble, water-soluble, and any optional oil-soluble deliverables.

In 310, a monolayer surfactant bound droplet combined mixture 312 is formed by combining a phospholipid and a polyethylene glycol derivative that together form a surfactant system of the monolayer surfactant bound droplets with an associating oil, a monolayer surfactant bound alcohol aliquot, alcohol-soluble deliverables, and any optional oil-soluble deliverables.

In 320, the monolayer surfactant bound droplet combined mixture 312 is stirred and heated until the components are dissolved to form a dissolved monolayer surfactant bound droplet solution 324.

In 330, a continuous phase combined mixture 332 is formed by combining water, a sugar or sugar alcohol, hybrid-soluble deliverables including their aliquots of alcohol and water, and water-soluble deliverables.

In 340, the continuous phase combined mixture 332 is stirred and optionally heated until the components are dissolved or nearly dissolved to form a dissolved continuous phase 344.

In 350, the dissolved monolayer surfactant bound droplet solution 324 is combined with the dissolved continuous phase 344 with stirring at atmospheric pressure to form a microemulsion.

The following examples illustrate one or more preferred embodiments of the invention. Numerous variations may be made to the following examples that lie within the scope of the invention.

EXAMPLES

Example 1: Constituents of the Intra-Oral, Microemulsion Including Astragaloside IV, Cycloastragenol, and Pregnenolone as Nonderivatized Alcohol-Soluble Deliverables A microemulsion was prepared having a 5 mL total volume. The deliverables of the microemulsion included 10 mg of astragaloside IV, 10 mg of cycloastragenol, and 10 mg of pregnenolone as the alcohol-soluble deliverables; 750 mg of He Shou Wu Tincture as a liquid including 350 mg of solids, water, and ethanol; 200 mg of Zhi Gan Cao (honey prepared licorice root) tincture as a liquid including 40 mg of solids, water, and ethanol; 500 mg of ashwagandha tincture as a liquid including 10 mg solids, water, and ethanol; 25 mg of ashwagandha in solid powder form, 62 mg of Chinese Ginseng in solid powder form; 15 mg of American Ginseng in solid powder form; and 75 mg of Fermented Korean Ginseng in solid paste form. The hybrid-soluble deliverables maintained an herb strength of approximately 1:5 herb to the water/ethanol solvent.

The microemulsion also included 300 to 700 mg of PC; 200 to 700 mg of associating oil including MCT, orange, and lemon oils; 1700 to 2200 mg total ethanol; 3200 to 4000 mg of glycerol; and minor amounts of sweetener. TPGS was included to provide the desired physical structures in the microemulsion. In addition to these ingredients, the microemulsion included enough water to provide a total volume of 5 mL.

Example 2: a Method of Making an Intra-Oral, Microemulsion

The monolayer surfactant bound droplet phase of the microemulsion was made by combining the alcohol-soluble deliverables with the PC, TPGS, associating oil, and 800 to 1300 mg of ethanol as referenced in Example 1. The resulting liquid and solid mixture was stirred and heated until the liquids and solids were dissolved.

The continuous phase of the microemulsion was made by combining the hybrid-soluble deliverables including their aliquots of alcohol and water, water-soluble deliverables, glycerol, and water as referenced in Example 1. The resulting liquid and solid mixture was stirred until the liquids and solids dissolved or nearly dissolved.

The monolayer surfactant bound drop phase was then combined with the continuous phase with stirring at atmospheric pressure to form 5 mL of microemulsion. Stirring was provided by a magnetic stirring bar, but could otherwise be provided.

Example 3: Bioavailability Uptake and Duration for Intra-Oral Delivery of Nonderivatized Pregnenolone Via the Microemulsion A microemulsion was formed in accord with Example 2 including 10 mg of each of the nonderivatized alcohol-soluble deliverables astragaloside IV, cycloastragenol, and pregnenolone.

On an empty stomach, both male and female subjects placed 5 mL of the microemulsion under their tongue. The subjects held the microemulsion under the tongue for approximately 30-seconds to 2-minutes before swallowing the microemulsion.

Blood samples were collected before the microemulsion was administered intra-orally and at varying time intervals between 30- and 300-minutes after administration of the microemulsion to the subjects. The collected blood samples were analyzed for the plasma concentration of pregnenolone. As the astragaloside IV and cycloastragenol are solubilized in the monolayer surfactant bound droplets of the microemulsion in addition to the pregnenolone, a similar delivery profile to pregnenolone for the astragaloside IV and the cycloastragenol nonderivatized alcohol-soluble deliverables into the subjects' bloodstream would be expected.

Prior to microemulsion administration to the subjects, baseline plasma pregnenolone concentrations were determined for each subject and subtracted from the concentration values measured during the study, thus the reported pregnenolone plasma concentrations are the increase over baseline.

Figure 4:
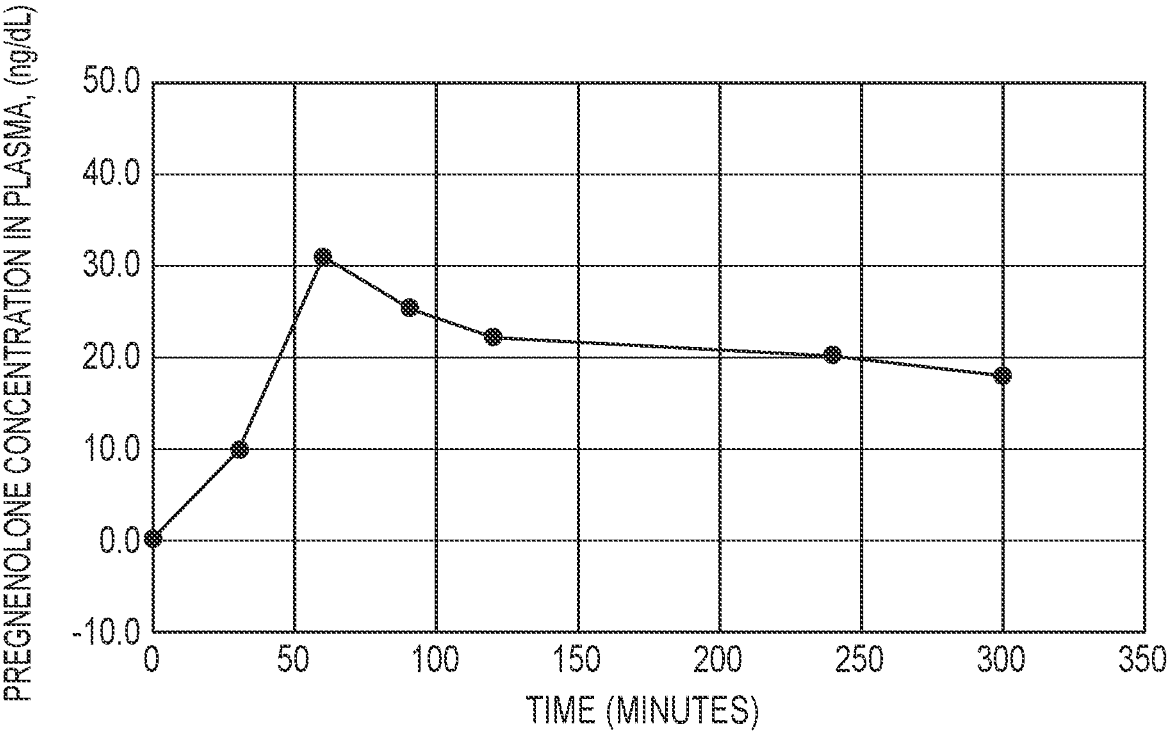
FIG. 4 provides the average results of a bioavailability uptake and duration analysis in graphical form for pregnenolone in response to the intra-oral dosing of the microemulsion to the subjects.

FIG. 4 provides the average results of a bioavailability uptake and duration analysis in graphical form for pregnenolone in response to the intra-oral dosing of the microemulsion to the subjects. The measured plasma pregnenolone concentration values in nanograms per decalitre (ng/dL) for the individual subjects averaged to provide FIG. 4 are presented below in Table I.

TABLE I

| Minutes Post-Administration | Male 1 | Female 1 | Male 2 | Average |
|---|---|---|---|---|
| 30 | 21.4 | 0.6 | 7.4 | 9.8 |
| 60 | 19.3 | 49.4 | 24.1 | 30.9 |
| 90 | 10.2 | 43.5 | 21.9 | 25.2 |
| 120 | 9.2 | 37.4 | 19.5 | 22.0 |
| 240 | 9.9 | 32.7 | 17.8 | 20.1 |
| 300 | 9.1 | 28 | 16.4 | 17.8 |

The increase in plasma pregnenolone concentration for the subjects in response to the intra-oral administration of the microemulsion over the timeframe of the study was significant. The average plasma pregnenolone concentration of the subjects reached a maximum approximately 60-minutes post-administration with a Cmax of 30.9 ng/dL, and after a relatively slow decline maintained a relatively level plasma concentration from 120-minutes post-administration until the 300-minute study end time. Even the lowest-absorbing Male 1 subject experienced an at least 9 ng/dl increase in pregnenolone bloodstream concentration over baseline for the 300-minute duration of the study. Also of interest in this regard is the Female 1 subject who experienced a 28 ng/dl to 49 ng/dl in bloodstream pregnenolone concentration from 60-minutes post intra-oral administration through the 300-minute study end.

The ability of the microemulsion to rapidly deliver alcohol-soluble deliverables, such as non-derivatized pregnenolone, to the bloodstream of a subject after intra-oral delivery was established.

Example 4: Comparative Bloodstream Uptake Rates and Concentrations for Nonderivatized Pregnenolone A liquid form conventional oil blend delivery system was formed by combining 10 mg of nonderivatized pregnenolone in 5 mL of MCT oil. A solid form conventional delivery system using a "00" veggie capsule was formed by combining 10 mg of nonderivatized pregnenolone with 290 mg of rice flour and administered with 5 mL of distilled water. The microemulsion as formed in accord with Example 2 including 10 mg of each of the nonderivatized alcohol-soluble deliverables astragaloside IV, cycloastragenol, and pregnenolone was used for comparison.

On an empty stomach, a male subject placed 5 mL of the oil blend delivery system under their tongue. The subject held the oil blend delivery system under their tongue for approximately 30-seconds to 2-minutes before swallowing the oil blend. On an empty stomach, a male subject immediately swallowed the solid form capsule. As previously discussed in Example 3, on an empty stomach, both male and female subjects placed 5 mL of the microemulsion under their tongue. The subjects held the microemulsion under the tongue for approximately 30-seconds to 2-minutes before swallowing the microemulsion.

Blood samples were collected before administration of the delivery systems to the subjects and at varying time intervals between 30- and 300-minutes post-administration of the delivery systems to the subjects. The collected blood samples were analyzed for the plasma concentration of pregnenolone.

A plasma pregnenolone concentration value of 1.2 ng/dL was added to each increase over baseline value determined to provide an adjusted baseline concentration as it is not uncommon for pregnenolone concentrations to slightly decrease throughout the day. The 1.2 ng/dl value was added to remove negative increase over baseline values, which would otherwise result in incorrect Bioavailability values due to the calculation method.

Figure 5:
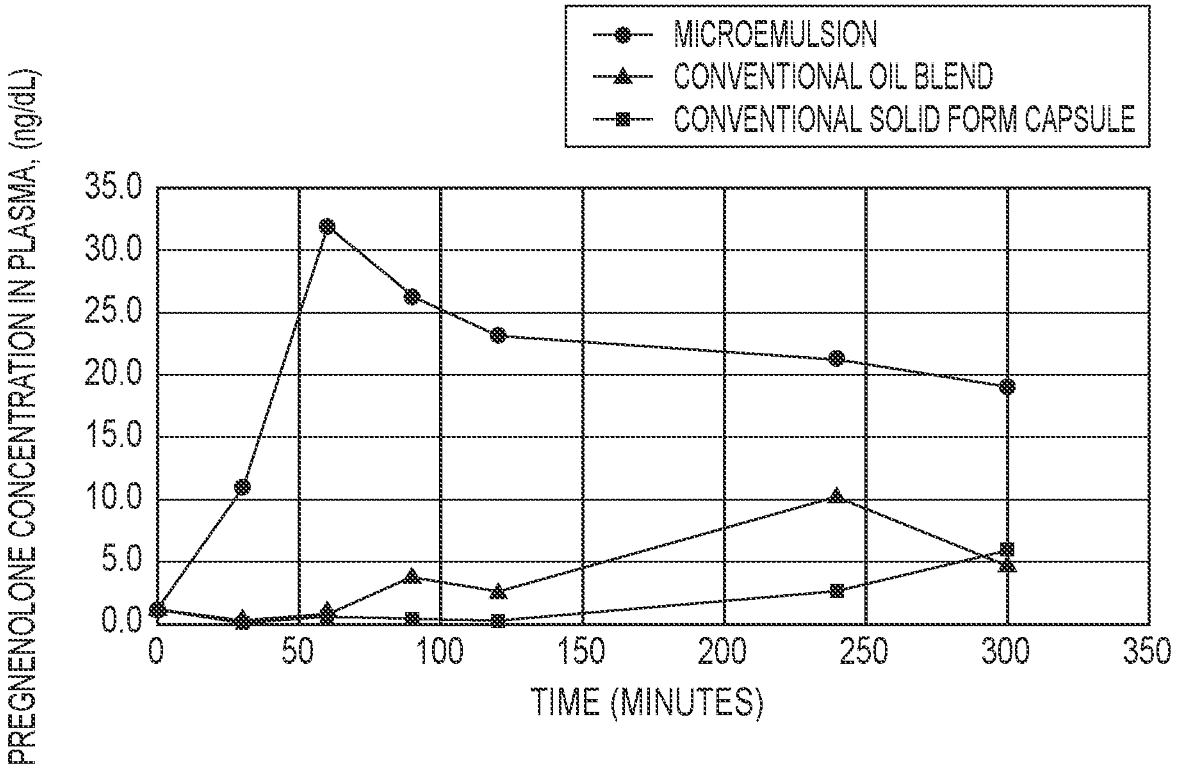
FIG. 5 provides comparative results of a bioavailability uptake and duration analysis in graphical form for pregnenolone in response to the liquid form conventional oil blend delivery system, the solid form capsule conventional delivery system, and the intra-oral dosed microemulsion.

FIG. 5 provides comparative results of a bioavailability uptake and duration analysis in graphical form for pregnenolone in response to the liquid form conventional oil blend delivery system, the solid form capsule conventional delivery system, and the intra-oral dosed microemulsion. Average values are used for the intra-oral dosed microemulsion due to multiple subjects. The plasma pregnenolone concentration values over the 1.2 ng/dL adjusted baseline in nanograms per milliliter (ng/dL) for the microemulsion (average values) and for the two conventional delivery systems used to provide FIG. 5 are presented below in Table II.

TABLE II

| Minutes Post-Administration | Micro-emulsion Average | Conventional Oil Blend | Conventional Solid Form Capsule |
|---|---|---|---|
| 0 | 1.2 | 1.2 | 1.2 |
| 30 | 11.0 | 0.1 | 0 |
| 60 | 32.1 | 0.8 | 0.6 |
| 90 | 26.4 | 3.9 | 0.4 |
| 120 | 23.2 | 2.6 | 0.3 |
| 240 | 21.3 | 10.2 | 2.7 |
| 300 | 19.0 | 4.7 | 6.0 |

The superiority of the microemulsion at delivering pregnenolone to the bloodstream in relation to the conventional oil and solid phase delivery systems is apparent from a blood uptake perspective. The pregnenolone delivery profile provided by the intra-oral administered microemulsion differed substantially from that of the conventional oil blend, as the conventional oil blend provided a Cmax of approximately 10 ng/dL 240-minutes post administration, but substantially no bloodstream concentration at the 60-minute Cmax of the microemulsion—with the 1.2 ng/dl addition, values less than 1.2 ng/dL equate to substantially no delivery to the bloodstream.

In contrast to the delivery profile of the microemulsion, the delivery profile of the oil blend did not begin to show blood delivery until approximately 90-minutes post-administration, underwent a slow increase to the 240-minute Cmax, and then sharply declined until the 300-minute study end time. The delivery profile from the conventional solid form capsule was more similar to the oil blend than to the intra-oral dosed microemulsion. The conventional solid form capsule provided a Cmax of 6 ng/dl at the 300-minute study end time reflecting an extremely low and slow pregnenolone uptake profile and provided substantially no bloodstream pregnenolone delivery until 240-minutes post-administration.

The "low to high" delivery profiles of the conventional delivery systems in relation to the "high to low" delivery profile of the microemulsion is believed to illustrate the difference between the microemulsion's enhanced ability to intra-orally deliver pregnenolone to the bloodstream of a subject verses the conventional oil and solid form delivery systems' favored gastrointestinal bloodstream delivery pathway. The substantially more rapid (60-minute Cmax) blood uptake provided by the microemulsion in relation to the conventional delivery systems (240- and 300-minuted Cmax) shows the microemulsion's ability to substantially "bypass" the gut. Both conventional delivery systems are believed to substantially deliver the alcohol-soluble species via the gut while the microemulsion is believed to substantially intra-orally deliver the alcohol-soluble species via the mouth and the esophagus.

From a comparative delivery perspective, at the 240-minute post-administration Cmax for the conventional oil blend, the conventional oil blend provided a bloodstream pregnenolone concentration of 10 ng/dl while the microemulsion provided 21 ng/dl-approximately twice as much pregnenolone. The conventional solid form capsule was inferior to the oil blend, providing a maximum bloodstream concentration of 6 ng/dL 300-minutes post administration where the nanoemulsion provided a 19 ng/dl concentration—more than three times as much pregnenolone. The ability of the microemulsion to rapidly deliver pregnenolone at a significantly enhanced uptake to a subject in relation to the conventional delivery systems was established.

The microemulsion can provide a subject with a pregnenolone plasma concentration of at least 10 to 25 ng/dl over a baseline pre-administration concentration, preferably at least 20 to 28 ng/dL, within 60-minutes of intra-oral administration. These values have the 1.2 ng/dl adjustment removed, and thus represent the measured increase in plasma concentration provided by the microemulsion to a subject over the measured pre-administration baseline and thus internalize any normal decrease in pregnenolone concentrations over the 60-minute duration.

Example 5: Total Exposure of Pregnenolone

Figure 6:
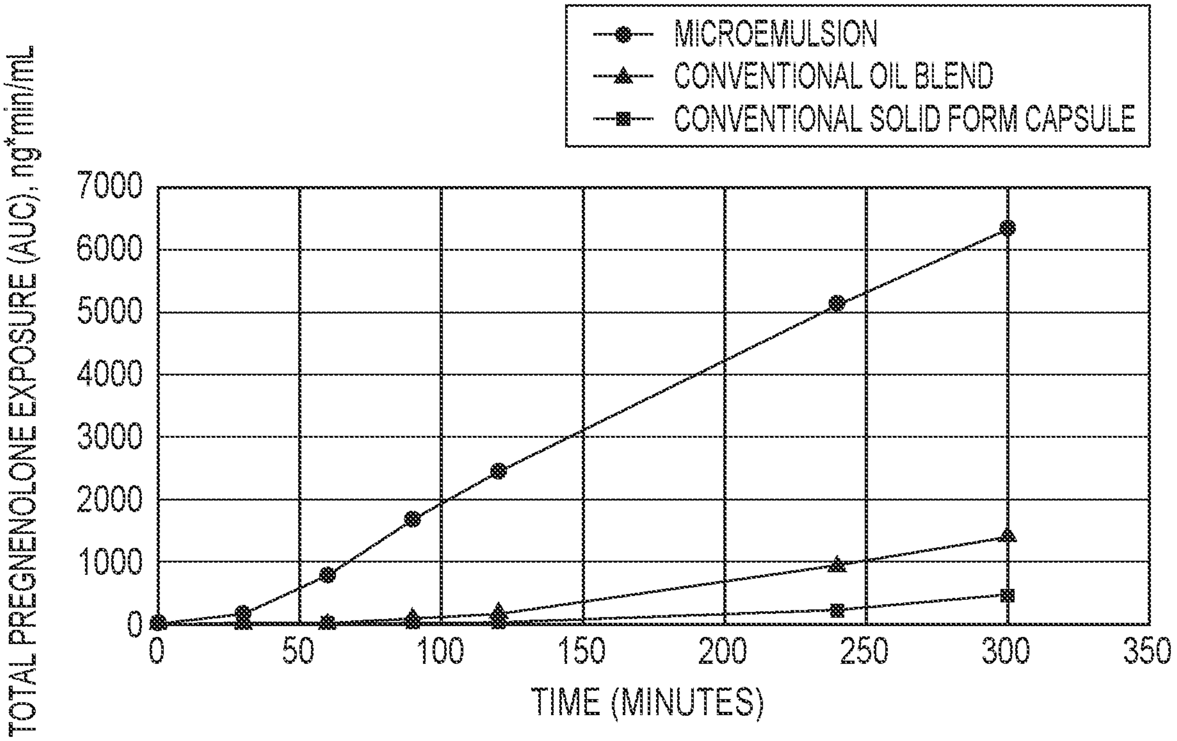
FIG. 6 provides cumulative Area Under the Curve (AUC) values in ng* (min/mL) in graphical form as calculated in Table III from the bloodstream pregnenolone concentrations previously provided in Table II.

FIG. 6 provides cumulative Area Under the Curve (AUC) values in ng* (min/dL) in graphical form as calculated and provided in Table III from the bloodstream pregnenolone concentrations previously provided in Table II. The calculated AUC values provide a measure of the cumulative amount of pregnenolone in the bloodstream, thus total pregnenolone exposure across a time duration.

TABLE III

| Minutes Post-Administration | Micro-emulsion Average AUC | Conventional Oil Blend AUC | Conventional Solid Form Capsule AUC |
|---|---|---|---|
| 30 | 183 | 19 | 18 |
| 60 | 830 | 33 | 27 |
| 90 | 1708 | 103 | 42 |
| 120 | 2452 | 201 | 52 |
| 240 | 5126 | 969 | 232 |
| 300 | 6337 | 1416 | 493 |

At 60-minutes post-administration, the cumulative delivery of the oil blend was 33, the cumulative delivery of the solid form capsule was 27, and the cumulative delivery of the microemulsion was 2308. At the 300-minutes post-administration study end, the cumulative delivery of the oil blend was 1416, while the cumulative delivery of the microemulsion was 6337. The conventional solid form capsule performed worse than the conventional oil blend from a cumulative delivery perspective after 300-minutes by providing a cumulative delivery value of 493, thus approximately 3-times less than the conventional oil blend and approximately 13-times less than the microemulsion. The ability of the microemulsion to provide significantly enhanced cumulative delivery of an alcohol-soluble deliverable, such as pregnenolone, to a subject in relation to the conventional delivery systems was established.

Example 6: Relative Pregnenolone Bioavailability

Relative nonderivatized pregnenolone bioavailability between the conventional and microemulsion delivery systems was determined at different times after administration to the subjects using the AUC values from Table III by multiplying the AUC up to the selected time point by the amount of nonderivatized pregnenolone in the selected delivery system and dividing by a control value likewise calculated, thus (AUC1*delivery system1)/(AUCcontrol*delivery system control) at the selected time. As this calculation divides the total amount of pregnenolone delivered by the numerator delivery system by the total amount of pregnenolone delivered by the denominator delivery system at a selected time, the resulting values relate to how many times more pregnenolone was delivered by the numerator delivery system in relation to the denominator delivery system at the selected time.

The results from the AUC calculations are provided below in Table IV for the microemulsion as the numerator and the conventional oil blend or the solid form delivery systems as the denominator.

TABLE IV

| Time Minutes | Bioavailability Oil Blend | Bioavailability Solid Form |
|---|---|---|
| 30 | 9 | 10 |
| 60 | 25 | 30 |
| 90 | 16 | 41 |
| 120 | 12 | 47 |
| 240 | 5 | 22 |
| 300 | 4 | 13 |

At 60-minutes after administration, the microemulsion delivered nearly 25-times as much pregnenolone on a cumulative basis to the bloodstream of the subject as the oil blend and nearly 30-times as much pregnenolone to the subject as the solid form capsule from the same 10 mg of administered nonderivatized pregnenolone. After five-hours, the microemulsion delivered approximately 4-times as much pregnenolone on a cumulative basis to the bloodstream as the oil blend and approximately 13-times as much as the solid form capsule—thus establishing the substantially superior pregnenolone delivery performance of the microemulsion in relation to the conventional delivery systems. These calculated values confirm the ability of the microemulsion to rapidly deliver and maintain therapeutically effective bloodstream concentrations of pregnenolone after administration to a subject in relation to the conventional delivery systems.

The microemulsion was able to deliver from 20 to 30 times more nonderivatized hormone to the bloodstream of a subject on a cumulative basis after one hour than the conventional delivery systems. The microemulsion also was able to deliver from 2 to 10 times more nonderivatized hormone to the bloodstream of a subject on a cumulative basis after five hours than the conventional delivery systems.

Example 7: Pregnenolone Bloodstream Delivery Efficiency

Each of the three delivery systems included 10 mg of nonderivatized pregnenolone. When the amount of nonderivatized pregnenolone administered in each delivery system is considered, the bloodstream delivery efficiency of the conventional liquid and solid form delivery systems is very poor.

From a bloodstream delivery efficiency perspective, the microemulsion delivered greater than 20-times as much of the administered nonderivatized pregnenolone to the bloodstream than the conventional oil blend or the solid form capsule after one hour. After five hours, the microemulsion delivered more than four times as much pregnenolone to the bloodstream in relation to the conventional oil blend and more than 10 times as much pregnenolone to the bloodstream in relation to the conventional solid capsule form.

For a five-hour period, for the oil blend to approximate the cumulative pregnenolone delivery of the microemulsion, one would seemingly have to administer 20 mL of the oil blend including 40 mg of nonderivatized pregnenolone to match what 5 mL of the microemulsion including only 10 mg of nonderivatized pregnenolone could deliver. Similarly, more than 10 solid form capsules would need to be consumed to approximate the pregnenolone delivery of the microemulsion. Thus, the oil blend would waste 30 mg of nonderivatized pregnenolone per dose while requiring consumption of an undesirable quantity of oil, while the solid form would waste something approximating 120 mg of nonderivatized pregnenolone per dose and basically require a handful of capsules to be administered.

The microemulsion provides a significant production cost advantage over the conventional oil blend as in relation to the microemulsion, approximately 75% of the pregnenolone included in the oil blend is "wasted" as it fails to provide additional relevant bloodstream concentration. In relation to the oil blend, the ability of the microemulsion to efficiently deliver intra-orally administered nonderivatized pregnenolone to the bloodstream of a subject was established. The conventional solid form delivery system would be impractical due to the approximately 92% loss of pregnenolone and capsule volume required.

To provide a clear and more consistent understanding of the specification and claims of this application, the following definitions are provided.

Intra-oral delivery means that a substantial portion of the delivery into the bloodstream that occurs upon oral administration of the liquid including the deliverable occurs by transmucosal absorption through the mouth, throat and esophagus before the liquid reaches the stomach. For intra-oral delivery, the subject takes the composition into the oral cavity, holds the composition for a time within the oral cavity, and then swallows the remaining composition. For droplets to be considered suitable for intra-oral delivery, the average droplet diameter is at most 125 nm. Intra-oral delivery is believed to increase with decreasing average droplet diameter, with average droplet diameters of approximately 25 nm being preferred.

An alcohol-soluble deliverable is a deliverable that is insoluble in water and has a greater solubility in ethanol than in medium chain triglyceride (MCT) oils. For example, the nonderivatized hormone DHEA is soluble in ethanol up to approximately 150 mg/mL, thus being freely soluble in ethanol, while having a solubility in MCT oil of approximately 10 mg/mL, thus being only sparingly soluble. Alcohol-soluble deliverables are preferably pharmacologically active, more preferably are a drug or a supplement, and neither include nor are water. Thus, liquids and solids may exist that technically are soluble in alcohol, but because they also are soluble in water or more or equivalently soluble in MCT oils than in ethanol are not "alcohol-soluble deliverables".

An oil-soluble deliverable is a deliverable that is insoluble in water and soluble in medium chain triglyceride (MCT) oils at 50 mg/mL and higher, preferably 100 mg/mL and higher. Oil-soluble deliverables are generally soluble in MCT oils at room temperature and are freely or very soluble in MCT oils at temperatures of 70 degrees Celsius and greater. The term "generally soluble in MCT oils at room temperature" is used because some high purity oil-soluble deliverables are sparingly soluble in MCT oils at room temperature, but are freely or very soluble in the MCT oils above 70 degrees Celsius, and once solubilized in the MCT oils at elevated temperature, will remain solubilized at room temperature. Oil-soluble deliverables are preferably pharmacologically active, more preferably are a drug or a supplement, and neither include nor are water. Thus, liquids and solids may exist that technically are soluble in oil, but because they also are soluble in water or not sufficiently soluble in MCT oils are not "oil-soluble deliverables".

Radix *Astragali* root extracts include direct solvent extracts of the Radix *Astragali* root, such as astragaloside IV, and chemically transformed direct extracts of the Radix *Astragali* root, such as cycloastragenol, that are alcohol-soluble deliverables. Thus, Radix *Astragali* root extracts exclude chemically derivatized versions of Radix *Astragali* root extracts derivatized to make them sparingly soluble, slightly soluble, or soluble in water or MCT oil.

Nonderivatized hormones are chemically identical to hormones made by the human body and are not synthetically modified with fatty esters or other pendant groups.

Directly solubilize the nonderivatized hormone or Radix *Astragali* root extract means that unlike in conventional systems, the nonderivatized hormone or Radix *Astragali* root extract does not require synthetic conversion to an esterified or otherwise derivatized state to be solubilized, thus the microemulsion "directly solubilizes" the nonderivatized hormone or Radix *Astragali* root extract.

Phosphatidylcholine (PC) molecules are a subset of the larger set of phospholipids and are commonly used to form liposomes in water. When placed in water without other constituents, the PC forms liposomes. The application of sufficient shear forces to the PC liposomes can reduce the bilayer liposome structures to monolayer structures, including micelles. PC has a head that is water-soluble and a tail that is much less water-soluble in relation to the head. PC is a neutral lipid, but carries an electric dipole moment of about 10 D between the head and the tail, making the molecule itself polar.

Tocopheryl polyethylene glycol succinate 1000 (TPGS) is generally considered a surfactant having a non-polar, oil-soluble "Vitamin E" tail and a polar, water-soluble polyethylene glycol head. TPGS is a member of the polyethylene glycol derivatives that also include polysorbate 20, 40, 60, and 80.

MCT oils are triglycerides whose fatty acids have an aliphatic tail of 6-12 carbon atoms.

Room temperature and pressure means from 20 to 27 degrees Celsius at approximately 100 kPa.

Solid means a substance that is not a liquid or a gas at room temperature and pressure. A solid substance may have one of a variety of forms, including a monolithic solid, a powder, a gel, or a paste.

Liquids are substances that are not a solid or a gas at room temperature and pressure. A liquid is an incompressible substance that flows to take on the shape of its container.

Solutions lack an identifiable interface between the solubilized molecules and the solvent. In solutions, the solubilized molecules are in direct contact with the solvent.

Solubilized means that the alcohol-soluble deliverable is in the solution of the droplet. When solubilized, dissociation (thus, liquid separation or solid formation) of the alcohol-soluble deliverable does not result in droplet average droplet diameters greater than 200 nm as determined by DLS and discussed further below, or by the formation of precipitated crystals of the alcohol-soluble deliverable visible with the naked eye. Thus, if either average droplet diameters greater than 200 nm or precipitated crystals visible to the naked eye form, the deliverable is not solubilized in the solution of the droplet. If a deliverable is not solubilized in the solution, it is insoluble in the solution. In many respects, solubility may be thought of as a concentration dependent continuum. For example, the following descriptive terms may be used to express solubility of a solute in a solvent (grams solid/mL of solvent) at 25 degrees Celsius:

| Descriptive Level | Parts solvent per 1 part of solute |
|---|---|
| Very Soluble | Less than 1 |
| Freely Soluble | From 1 to 10 |
| Soluble | From 10 to 30 |
| Sparingly Soluble | From 30 to 100 |
| Slightly Soluble | From 100 to 1000 |
| Very Slightly Soluble | From 1000 to 10,000 |
| Insoluble | More than 10,000 |

Dissociation occurs when a previously solubilized solid or liquid leaves a solution and is no longer in direct contact with a solvent of the solution. Dissociation of solids from the solvent occurs through recrystallization, precipitation, and the like. Dissociation of liquids from the solvent occurs through separation and the formation of a visible meniscus between the solvent and the dissociated liquid.

A shelf-stable microemulsion may be determined in one of two ways. One way to establish that a microemulsion stored in a sealed container substantially excluding air and moisture is shelf-stable is when dissociation of a solid does not occur and the oil phase droplets in the water do not change in average diameter by more than +/−20% at about 25 °C for a time period of at least 3 months to 2 years, preferably for a time period of at least 6 months to 2 years, and more preferably, for a time period of at least 1 year to 2 years. Another way to establish that a microemulsion is shelf-stable is when dissociation of a solid does not occur and the oil phase droplets in the water do not separate into a visibly distinct phase with a visible meniscus when stored in a sealed container substantially excluding air and moisture at about 25 °C for a time period of at least 6 months to 2 years, and more preferably, for a time period of at least 1 year to 2 years. Either dissociation type means that the microemulsion is not shelf-stable.

Emulsions are mixtures of two or more liquids that do not solubilize. Thus, one of the liquids carries droplets of the second liquid. The droplets of the second liquid may be said to be dispersed in a continuous phase of the first liquid. An interface, separation, or boundary layer exists between the carrier liquid (continuous phase) and the droplets of the second liquid. Emulsions may be macroemulsions, pseudo-emulsions, microemulsions, or nanoemulsions. The primary differences between macroemulsions, microemulsions, and nanoemulsions are the average diameter of the droplets dispersed in the continuous phase and the stability of the emulsion over time. Pseudo-emulsions are differentiated as solids are present in the emulsion.

The terms "emulsion" and "dispersion" are used interchangeably herein for convenience.

Droplets are formed by the hydrophobic "oil" phase of a microemulsion and are carried by the hydrophilic continuous phase. The exterior of the droplets is defined by a boundary layer that surrounds the volume of each liquid droplet. The boundary layer of a droplet defines the exterior surface of the droplets forming the dispersed oil phase of the microemulsion. The continuous phase of the microemulsion resides exterior to the boundary layer of the droplets, and thus, carries the droplets.

Macroemulsions are thermodynamically unstable but kinetically stable dispersions of oil in water, with oil being defined as any water-insoluble liquid. By thermodynamically unstable it is meant that once created, the macroemulsion is always reverting to the original, immiscible state of the oil and water constituents (demulsification), but this break down is slow enough (thus, kinetically "stable") that the macroemulsion may be considered stable from an intended use practicality perspective. Macroemulsions scatter light effectively and therefore appear milky because their droplets are greater in diameter than the wavelength of visible light. The droplets of a macroemulsion usually have average droplet diameters from 10 to 50 micrometers. The IUPAC definition of a macroemulsion is an "emulsion in which the droplets of the dispersed phase have diameters from approximately 1 to 100 micrometers. Macro-emulsions comprise large droplets and thus are "unstable" in the sense that the droplets sediment or float, depending on the densities of the dispersed phase and dispersion medium."

Pseudo-emulsions are dispersions of oil in water, with oil being defined as any water-insoluble liquid, including tiny (micronized) solid granules that are not fully solubilized in the oil droplets. The term "pseudo-emulsion" is used as these mixtures are not true emulsions as the solid granules are not fully solubilized into the droplets. The droplets of a pseudo-emulsion have an average droplet diameter of 1 to 20 micrometers, thus being a "solid granule modified macroemulsion".

Microemulsions are thermodynamically stable dispersions of oil in water, with oil being defined as any water-insoluble liquid. Microemulsion are made by simple mixing of the components. Thus, microemulsions spontaneously form and do not require high shear forces. Unlike macroemulsions, microemulsions do not substantially scatter light. The IUPAC definition of a microemulsion is a "dispersion made of water, oil, and surfactant(s) that is an isotropic and thermodynamically stable system with dispersed domain diameter varying approximately from 1 to 100 nm, usually 10 to 50 nm." Thus, the droplets of a microemulsion are approximately three orders of magnitude smaller than the droplets of a macroemulsion and are thermodynamically stable.

Nanoemulsions have average droplet diameters from 10 to 125 nanometers, thus being at least an order of magnitude smaller in average droplet diameters than macro- and pseudo-emulsions. Transparent nanoemulsions have average droplet diameters from 10 to 100 nanometers. Nanoemulsions are made with mechanical, high shear forces. While the average droplet diameter of nanoemulsions and microemulsions formally overlap, in practice, the average droplet diameter of a nanoemulsion is or becomes larger than those of a microemulsion, as lacking the thermodynamic stability of a microemulsion, the average droplet diameter of the nanoemulsion is forever increasing. It is possible to apply the high shear forces required to form a nanoemulsion to a composition capable of forming a thermodynamically stable microemulsion, however, this will result in a microemulsion as the composition would have "self-assembled" without the high shear forces to form the microemulsion.

Continuous phase means the portion of a microemulsion that carries the droplets. For example, the microemulsions (non-polar "oil" droplets in polar continuous "water" phase) addressed herein have oil/alcohol droplets including the alcohol-soluble deliverable to be delivered carried in a polar continuous phase. While the words "water" and "oil" are used, the "water" can be any liquid that is more polar than the "oil" (such as a polar oil), and the "oil" can be any liquid that is less polar than the "water". Thus, the terms "polar continuous phase" and "water continuous phase" are synonymous, unless water is specifically being discussed as one of the microemulsion components.

Average particle or droplet diameter is determined by dynamic light scattering (DLS), sometimes referred to as photon correlation spectroscopy. The determination is made between 20° and 25° Celsius. One example of an instrument suitable for average particle diameter determination is a Nicomp 380 ZLS particle sizer as available from Particle Sizing Systems, Port Richey, FL. DLS can determine the diameter of particles in a liquid by measuring the intensity of light scattered from the particles to a detector over time. As the particles move due to Brownian motion the light scattered from two or more particles constructively or destructively interferes at the detector. By calculating the autocorrelation function of the light intensity and assuming a particle distribution, it is possible to determine the sizes of particles from 1 nanometer (nm) to 5 micrometers (μm). The instrument is also capable of measuring the Zeta potential of particles/droplets.

Microemulsion viscosity is determined using a Gilmont Falling Ball Viscometer with a number three (#3) tube size equipped with a tantalum ball. Such viscometers may be obtained, for example, from COLE-PARMER®, 625 East Bunker Ct Vernon Hills, IL. Viscosity determinations were made at 19 degrees Celsius using an approximately 7 mL sample. The tantalum ball density was 16.6 g/mL and the viscometer constant for tube #3 was 35. The equation used to determine viscosity was $\mu=K(\rho t-\rho)t$, where μ is viscosity in cp, ρt is ball density, ρ is liquid density, and time is in minutes.

Ingestible means capable of being ingested through the mouth by a living mammal while edible means fit to be eaten, thus in contrast to being unpalatable or poisonous. Edible also means that the composition has less than the permitted amount of viable aerobic microorganisms and meets the American Herbal Products Association (AHPA) guidelines for metals, adulterants, toxins, residual solvents, and pesticides.

Subject refers to an animal, including, but not limited to, a primate (e.g., human, monkey, chimpanzee, gorilla, and the like), rodents (e.g., rats, mice, gerbils, hamsters, ferrets, and the like), lagomorphs, swine (e.g., pig, miniature pig), equine, canine, feline, and the like. Thus, the term "subject" may be used in reference, for example, to a mammalian subject, such as a male or female human.

Delivered "in combination" or "co-delivery," refers to the delivery of astragaloside IV, cycloastragenol, and pregnenolone concomitantly in one composition.

An "effective amount" means an amount of deliverable effective to provide telomerase activity enhancement in the cells or tissue of the subject, such that a desired result is achieved.

The described methods can be performed in any suitable order unless otherwise indicated or contradicted by context.

Where a range of values is provided, it is understood that each intervening value, to the tenth of the unit of the lower limit unless the context clearly dictates otherwise, between the upper and lower limit of that range, and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the upper and lower limits, ranges excluding either or both of those included limits are also included in the invention.

Unless otherwise indicated, all numbers expressing quantities of ingredients, ratios, and the like used in the specification and claims are to be understood as indicating both the exact values as shown and as being modified by the term "about". Thus, unless indicated to the contrary, the numerical values of the specification and claims are approximations that may vary depending on the desired properties sought to be obtained and the margin of error in determining the values. At the very least, and not as an attempt to limit the application of the doctrine of equivalents to the scope of the claims, each numerical parameter should at least be construed considering the margin of error, the number of reported significant digits, and by applying ordinary rounding techniques.

The terms "a", "an", and "the" used in the specification claims are to be construed to cover both the singular and the plural, unless otherwise indicated or contradicted by context. No language in the specification should be construed as indicating any non-claimed element to be essential to the practice of the invention.

While various aspects of the invention are described, it will be apparent to those of ordinary skill in the art that other embodiments and implementations are possible within the scope of the invention. Accordingly, the invention is not to be restricted except considering the attached claims and their equivalents.

The invention claimed is:

1. An oral, liquid, microemulsion consisting essentially of:

a) a nonderivatized alcohol-soluble deliverable consisting essentially of a nonderivatized alcohol-soluble Radix *Astragali* extract and a nonderivatized alcohol-soluble hormone;

b) a hybrid-soluble deliverable selected from the group consisting of He Shou Wu tincture, Zhi Gan Cao (honey prepared licorice root), Ashwagandha, and combinations thereof;

c) a water-soluble deliverable selected from the group consisting of Ashwagandha, Chinese Ginseng, American Ginseng, Fermented Korean Ginseng, and combinations thereof;

d) monolayer surfactant bound droplets consisting essentially of:

i) the nonderivatized alcohol-soluble deliverables, ii) a surfactant system consisting essentially of a phospholipid and a polyethylene glycol derivative, wherein the polyethylene glycol derivative is selected from the group consisting of tocopheryl polyethylene glycol succinate 100, polysorbate 60, polysorbate 80, and combinations thereof, iii) an associating oil selected from the group consisting essentially of medium chain triglycerides (MCT), citrus oil, and combinations thereof, and iv) ethanol; and e) a continuous phase consisting essentially of three or more of glycerol, water, the hybrid-soluble deliverable, and the water-soluble deliverable, wherein the monolayer surfactant bound droplets have an average droplet diameter from 10 nanometers to 100 nanometers, and wherein the microemulsion is transparent and shelf-stable.

2. The microemulsion of claim 1, wherein the monolayer surfactant bound droplets have an average droplet diameter from 10 nanometers to 60 nanometers.

3. The microemulsion of claim 1, wherein the monolayer surfactant bound droplets have an average droplet diameter from 10 nanometers to 40 nanometers.

4. The microemulsion of claim 1 having a viscosity from 250 cp to 270 cp.

5. The microemulsion of claim 1, wherein the ratio of the polyethylene glycol derivative to the water to the glycerol is 1:2:4+/−20% by weight.

6. The microemulsion of claim 1, wherein the nonderivatized alcohol-soluble Radix *Astragali* extract consist essentially of astragaloside IV and cycloastragenol.

7. The microemulsion of claim 1, wherein the nonderivatized alcohol-soluble hormone consists essentially of a nonderivatized alcohol-soluble hormone selected from the group consisting of pregnenolone, DHEA, and combinations thereof.

8. The microemulsion of claim 1, wherein the nonderivatized alcohol-soluble hormone is selected from the group consisting of pregnenolone, DHEA, and combinations thereof.

9. The microemulsion of claim 1, wherein the nonderivatized alcohol-soluble Radix *Astragali* extract consists essentially of astragaloside IV and cycloastragenol and the one nonderivatized alcohol-soluble hormone is pregnenolone and at a ratio of astragaloside IV to cycloastragenol to pregnenolone is 1:1:1, by weight.

10. The microemulsion of claim 1, wherein the monolayer surfactant bound droplets further consist essentially of a hormone derivatized to have increased oil-solubility in relation to a nonderivatized alcohol-soluble form of the hormone.

11. The microemulsion of claim 1, wherein the phospholipid is selected from the group consisting of phosphatidylcholine (PC), phosphatidylethanolamine (PE), and combinations thereof.

12. The microemulsion of claim 1, wherein the ratio of the phospholipid to the nonderivatized alcohol-soluble deliverables is 1:0.08 to 0.17, by weight.

13. The microemulsion of claim 1, wherein the associating oil is selected from the group consisting of a medium chain triglyceride, a citrus oil, and combinations thereof.

14. The microemulsion of claim 1, wherein the ratio of the nonderivatized alcohol-soluble deliverables to the associating oil is 1:6 to 1:11, by weight.

15. The microemulsion of claim 1, wherein the ethanol is food grade ethanol.

16. The microemulsion of claim 1, wherein the ethanol is from 17% to 22% of the microemulsion, by weight.

17. The microemulsion of claim 1, wherein the ratio of the glycerol to the water in the continuous phase is from 1:0.3 to 1:0.7, by weight.

18. The microemulsion of claim 1, wherein the ratio of the phospholipid to the associating oil is from 1:0.8 to 1:1.4, by weight, and a ratio of the phospholipid to the alcohol is from 1:1.8 to 1:2.5, by weight.

19. The microemulsion of claim 1, wherein the phospholipid is 3% to 7% of the microemulsion, by weight, the polyethylene glycol derivative is 8% to 11% of the microemulsion, by weight, the associating oil is 2% to 7% of the microemulsion, by weight, the nonderivatized alcohol-soluble deliverable is 0.6% to 1.2% of the microemulsion, by weight, the hybrid-soluble deliverables are 2% to 6% of the microemulsion, by weight, the water-soluble deliverables are 2% to 4% of the microemulsion, by weight, the glycerol is 32% to 40% of the microemulsion, by weight, and the water is 15% to 21% of the microemulsion, by weight.

20. The microemulsion of claim 1, wherein the microemulsion is configured to provide a human a 10 ng/dl to 25 ng/dl plasma concentration increase of the nonderivatized alcohol-soluble hormone over a baseline plasma concentration within 60-minutes of administering the microemulsion to the human, where the nonderivatized alcohol-soluble hormone consists essentially of 10 mg of the nonderivatized alcohol-soluble hormone.

21. The microemulsion of claim 1, wherein the microemulsion is configured to provide a human at least twenty times the plasma concentration of the nonderivatized alcohol-soluble hormone than the nonderivatized alcohol-soluble hormone concentration provided by a conventional delivery system of the same amount of the nonderivatized alcohol-soluble hormone as the microemulsion within 60-minutes of administration to the human.

22. The microemulsion of claim 1, wherein the microemulsion is configured to provide a human at least twice the plasma concentration of the nonderivatized alcohol-soluble hormone than the nonderivatized alcohol-soluble hormone concentration provided by a conventional delivery system with the same amount of the nonderivatized alcohol-soluble hormone as the microemulsion within five hours of administration to the human.

23. A method of making the microemulsion of claim 1, the method consisting essentially of:

combining the nonderivatized alcohol-soluble deliverable with the surfactant system, the associating oil, and the ethanol to form a dissolved monolayer surfactant bound droplet solution;

combining the hybrid-soluble deliverable consisting essentially of aliquots of alcohol and water, the water-soluble deliverable, the glycerol, and the water with stirring to form a dissolved continuous phase; and combining the dissolved monolayer surfactant bound droplet solution and the dissolved continuous phase with stirring to form the microemulsion consisting essentially of the monolayer surfactant bound droplets carried by the continuous phase.

24. The method of claim 23, wherein alcohol-soluble constituents of the hybrid-soluble deliverables partition into the monolayer surfactant bound droplets of the microemulsion, and where water-soluble constituents of the hybrid-soluble deliverables partition into the continuous phase of the microemulsion.

25. The method of claim 23, wherein the combining consists essentially of stirring, heating, or stirring and heating to form the dissolved monolayer surfactant bound droplet solution.

26. The method of claim 25, wherein the combining with stirring to form the microemulsion is performed at room temperature and at atmospheric pressure.

27. The method of claim 26, wherein the combining with stirring to form the microemulsion is performed without high shear forces.

28. The method of claim 26, wherein the phospholipid is selected from the group consisting of phosphatidylcholine (PC), phosphatidylethanolamine (PE), and combinations thereof.

29. The method of claim 26, wherein a ratio of the phospholipid to the alcohol-soluble deliverables is 1:0.08 to 0.17 by weight in the microemulsion.

30. The method of claim 26, wherein the ethanol is food grade ethanol.

31. The method of claim 26, wherein the nonderivatized alcohol-soluble hormone is a nonderivatized alcohol-soluble hormone selected from the group consisting of pregnenolone, DHEA, and combinations thereof.

32. The method of claim 26, wherein the nonderivatized alcohol-soluble hormone is selected from the group consisting of pregnenolone, DHEA, and combinations thereof.

33. A method of intra-orally delivering the nonderivatized alcohol-soluble deliverable of claim 1 to the bloodstream of a human, the method consisting essentially of:

(a) administering intra-orally to the human the microemulsion of claim 1; and (b) delivering the nonderivatized alcohol-soluble deliverables to the bloodstream of the human, where within 60-minutes of the administering the microemulsion, a volume of the microemulsion where the nonderivatized alcohol-soluble hormone consists essentially of approximately 10 mg of pregnenolone provides the subject a bloodstream concentration increase of at least 19 ng/dl of the pregnenolone over a baseline bloodstream pregnenolone concentration.

34. The method of claim 33, wherein an at least 9 ng/dL increase in pregnenolone bloodstream concentration over the baseline is maintained for at least 300-minutes after the administering of the microemulsion to the human.

35. The method of claim 33, wherein the microemulsion provides the human at least twenty times the bloodstream concentration of the pregnenolone than a pregnenolone bloodstream concentration provided by a conventional delivery system with the same amount of the pregnenolone as the microemulsion within the 60-minutes of the administering.

36. The method of claim 34, wherein the microemulsion provides the human at least twice the bloodstream concentration of the pregnenolone than a pregnenolone bloodstream concentration provided by a conventional delivery system with the same amount of the pregnenolone as the microemulsion within five hours of the administering.

* * * * *